(12) United States Patent
Ishiura et al.

(10) Patent No.: US 7,407,797 B2
(45) Date of Patent: Aug. 5, 2008

(54) APPARATUS FOR MONITORING BIOLUMINESCENCE OF BIOLOGICAL SAMPLES

(75) Inventors: Masahiro Ishiura, Nagoya (JP); Kazuhisa Okamoto, Nagoya (JP); Kiyoshi Onai, Nagoya (JP); Takayoshi Furusawa, Mitaka (JP)

(73) Assignee: National University Corporation Nagoya University, Nagoya (JP)

( * ) Notice: Subject to any disclaimer, the term of this patent is extended or adjusted under 35 U.S.C. 154(b) by 715 days.

(21) Appl. No.: 10/985,955

(22) Filed: Nov. 12, 2004

(65) Prior Publication Data
US 2006/0057710 A1 Mar. 16, 2006

(30) Foreign Application Priority Data
Nov. 14, 2003 (JP) .............................. 2003-384577

(51) Int. Cl.
*C12M 1/34* (2006.01)
(52) U.S. Cl. ................. 435/288.7; 435/287.3
(58) Field of Classification Search .............. 435/288.7, 435/287.3
See application file for complete search history.

(56) References Cited

U.S. PATENT DOCUMENTS

| | | | | |
|---|---|---|---|---|
| 6,044,212 | A * | 3/2000 | Flavin et al. .................... | 703/6 |
| 6,107,050 | A * | 8/2000 | Alkon et al. .................. | 435/7.4 |
| 6,558,916 | B2 * | 5/2003 | Veerapandian et al. ........ | 435/29 |
| 6,576,476 | B1 * | 6/2003 | Taylor et al. ................ | 436/172 |
| 6,656,724 | B1 | 12/2003 | Heimberg et al. | |
| 6,977,722 | B2 * | 12/2005 | Wohlstadter et al. ........ | 356/246 |
| 2003/0092194 | A1 | 5/2003 | Gambini et al. | |
| 2006/0199260 | A1 * | 9/2006 | Zhang et al. ............. | 435/293.1 |

FOREIGN PATENT DOCUMENTS

| | | |
|---|---|---|
| DE | 199 25 161 A1 | 12/2000 |
| EP | 0 640 828 A1 | 3/1995 |
| EP | 1199569 A2 * | 4/2002 |
| JP | A-2001-523823 | 11/2001 |
| JP | A-310894 | 10/2002 |
| JP | A-2002-538477 | 11/2002 |
| WO | WO 91/01365 | 2/1991 |
| WO | WO 00/53720 | 9/2000 |
| WO | WO 01/63247 A2 | 8/2001 |

OTHER PUBLICATIONS

Takao, Kondo et al., "Biological Clock watched by eyes", Technical Report of Science Faculty of Nagoya University, 7$^{th}$, pp. 62-65, 1997.

* cited by examiner

*Primary Examiner*—Walter D. Griffin
*Assistant Examiner*—Lydia Edwards
(74) *Attorney, Agent, or Firm*—Oliff & Berridge, PLC

(57) ABSTRACT

An apparatus of monitoring the bioluminescence of organism samples comprises a culture part including a plurality of plates for putting plural organism samples and capable of cultivating said plural organism samples, a monitoring part for monitoring bioluminescences of said plural organism samples, a convey means for conveying said plural plates to said monitoring part, a control part for controlling a movement of said convey means and controlling a monitoring condition of the bioluminescence of said organism sample, and a computer for record and analysis, wherein said monitoring part, control part and computer are separated from each other.

13 Claims, 10 Drawing Sheets

A

B

A

B

C

A

B

| Luciferase (mol) | Bioluminescence (cps) | | | | | | | | | SD |
|---|---|---|---|---|---|---|---|---|---|---|
| | Det 1 | Det 2 | Det 3 | Det 4 | Det 5 | Det 6 | Det 7 | Det 8 | Mean | |
| Background | 89 | 56 | 66 | 55 | 59 | 67 | 63 | 79 | 66 | 12 |
| 1.0E-19 | 46 | 43 | 41 | 50 | 43 | 33 | 43 | 46 | 43 | 5 |
| 1.0E-18 | 592 | 445 | 460 | 482 | 503 | 460 | 532 | 523 | 500 | 49 |
| 1.0E-17 | 5,612 | 4,359 | 4,445 | 4,747 | 4,902 | 4,479 | 5,152 | 4,943 | 4,830 | 420 |
| 1.0E-16 | 57,932 | 43,269 | 45,523 | 47,567 | 49,678 | 44,674 | 51,265 | 49,791 | 48,712 | 4,645 |
| 1.0E-15 | 500,375 | 383,889 | 397,189 | 428,917 | 424,236 | 376,343 | 428,979 | 449,121 | 423,631 | 39,841 |
| 1.0E-14 | 3,979,566 | 3,063,881 | 3,271,126 | 3,323,822 | 3,472,439 | 3,052,814 | 3,769,135 | 3,510,164 | 3,430,368 | 324,717 |
| 1.0E-13 | 3,805,785 | 2,395,956 | 4,359,557 | 2,165,927 | 4,057,323 | 2,234,741 | 3,457,497 | 1,656,566 | 3,016,669 | 1,019,361 |

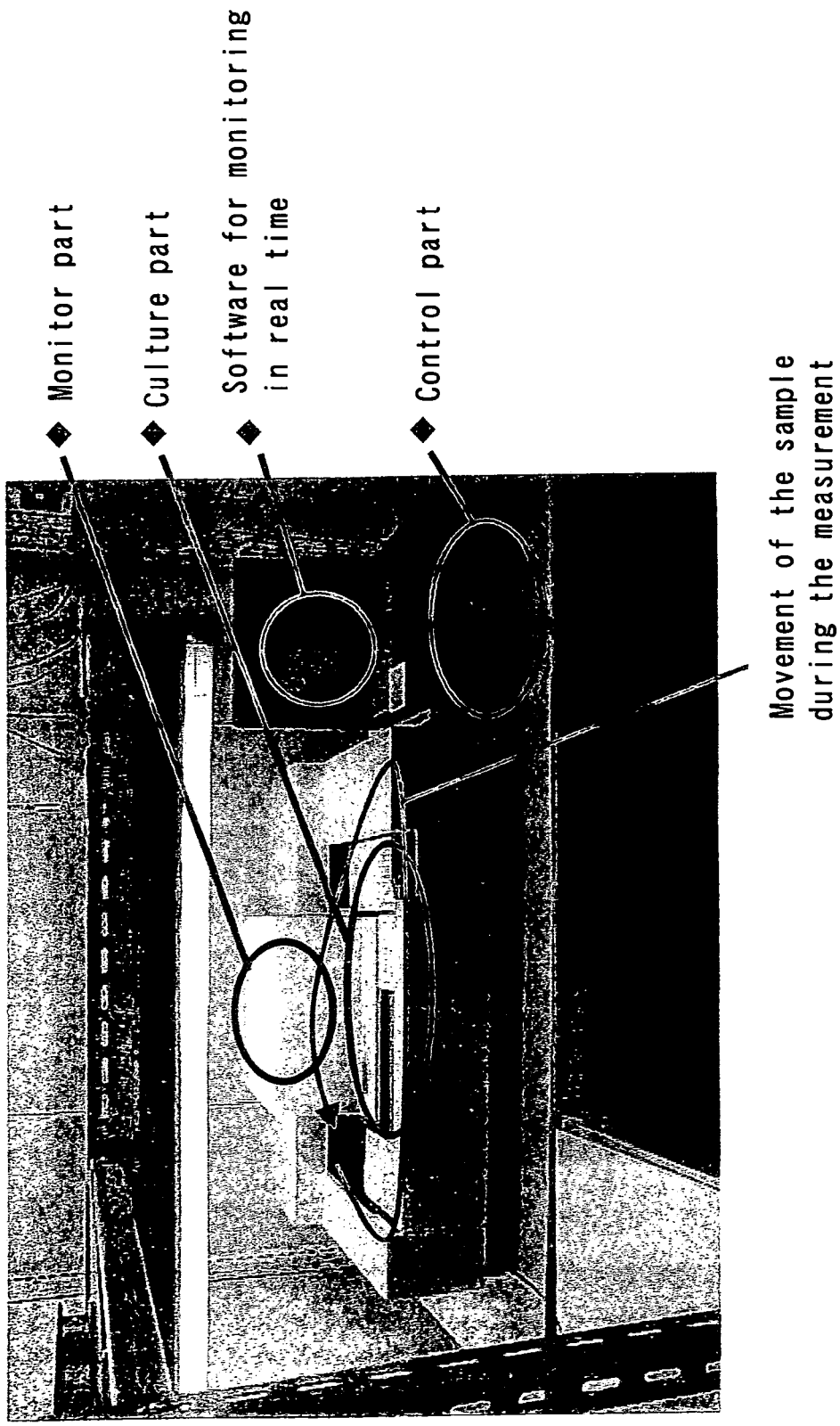

APPARATUS FOR MONITORING BIOLUMINESCENCE OF BIOLOGICAL SAMPLES

BACKGROUND OF THE INVENTION

1. Field of the Invention

This invention relates to an apparatus for monitoring a bioluminescence of a biological sample, and especially relates to an apparatus for monitoring a bioluminescence of a biological sample wherein a monitoring part and a control part are separated from each other.

2. Description of Related Art

In various organisms, all genome sequences are successively determined, and the importance on a cyclopaedically functional analysis of a genome based on genome information is increasing. As an effective method of the genome functional analysis are used a DNA array method and a proteomix method. In these methods, however, it is impossible to conduct functional analysis of all genes because the detection sensitivity is low. Also, it is required to destroy a cell in these methods because an experiment is carried out by using mRNA or protein as a material.

A method of monitoring a bioluminescence in real time (Kondo et al., 1993, Proc Natl Acad Sci USA, Vol. 90, p 5672-5676; Millar et al., 1992, Plant Cell, Vol. 4, p 1075-1087) is an epoch-making non-destructive measuring method capable of monitoring a gene expression in high sensitivity and accuracy without destroying a cell. This method of monitoring a bioluminescence in real time is a key method of cyclopaedically analyzing the genome function.

Heretofore, a scintillation counter used for monitoring a radiation is utilized in the monitoring of the bioluminescence. This method utilizing the scintillation counter adopts a stacker system wherein plural 96-well plates for putting a biological sample into each well are vertically stacked on a plate-setting portion of the monitoring apparatus with an exclusive guide. That is, according to this method, when plant-based biological samples requiring a light for their growing are monitored, plates including the sample and transparent plates including no sample are stacked alternately and a light is applied from their side faces (Strayer et al., 2000, Science, Vol. 289, p 768-771).

As this method is further explained, two stackers are first provided, and the plates including the sample and the transparent plates including no sample are alternately stacked in one of the stackers as previously mentioned and the other stacker is kept at an empty state containing no plate. In the monitoring of the luminescence form the plant-based biological samples requiring a light for their growing, a light is irradiated from their side faces, whereby the light is irradiated to the plate to be tested from a space formed between the transparent plates.

The monitoring is carried out by taking out a bottom plate from the stacked plates and feeding into a measuring darkroom, and the plate after the monitoring is moved into a bottom of the other stacker, and then the monitoring of a newly bottom plate in the stacked plates of the stacker is carried out. After the monitoring of all plates is completed, these plates are taken out from the bottom of the stacker containing the measured plates and returned to the stacker having no plates to be tested in turn to render into a state prior to the monitoring. The monitoring is carried out by repeating the above procedure. Since a temperature is raised by the light source near to the plates, the problem of raising the temperature is somewhat mitigated by blowing air to the batch of the plates stacked through a fan.

In the bioluminescence monitoring of blue-green bacterium, a large scale apparatus of monitoring the bioluminescence is developed by Kondo and Ishiura, whereby a fully automatic monitoring of the bioluminescence on a large number of test samples is attained at a time (Kondo et al., 1994, Journal of Bacteriology, Vol. 176, p 1881-1885; Kondo et al., 1994, Science, Vol. 266, p 1233-1236). In this apparatus, since a chilled CCD camera is used for monitoring the bioluminescence, the monitoring sensitivity is low as compared with the use of the scintillation counter.

In the above method using the scintillation counter, however, it has been confirmed that an amount of light irradiated to each plate and an amount of light irradiated into each well within the plate are very non-uniform and the cultivation becomes non-uniform and hence a large scattering is caused in the monitored result. Also, it has been confirmed that since it is necessary to approach the light source to the sample for ensuring the amount of the light required for the growth, water included in the material to be tested is dewed in an inside of a seal attached to the plate by heat generated from the light source to largely scatter the monitored result. Further, it has been confirmed that the comparison and investigation of data every experience are not easy because the monitoring number per unit time changes as the number of the plates to be tested changes.

The apparatus for monitoring the bioluminescence of the samples is especially adaptable to a method for monitoring the bioluminescence in real time wherein the variation of the gene expression in a living cell of an organism incorporated with an emission gene is continuously monitored. This real-time method is an experiment method considerably effective for cyclopaedically separating a mutant related to the control of expression of any key gene, which is a powerful card for a cyclopaedical genome function analysis in the post-genomic era. Up to now, however, there is not developed an apparatus utilizing the merits of the real-time method to the utmost to cope with the large-scale monitoring.

Although the scintillation counter is generally used in the monitoring of the luminescence of organism samples, it is difficult to monitor plant-based organism samples under uniform growth cultivating conditions (especially, the light condition) because the light is required for the growth.

In the method of combining the sample cultivating and transferring apparatus and the scintillation counter, a large space is required for setting the apparatus and the cost becomes high. Moreover, since a control computer included in the scintillation counter is weak to a high temperature, the monitoring could be only carried out under a temperature environment of 15-35° C.

SUMMARY OF THE INVENTION

It is, therefore, an object of the invention to provide an apparatus for monitoring a bioluminescence of an organism sample which can monitor the luminescence in a high reliability while growing the organism samples under the uniform conditions.

In order to achieve the above object, the inventors have strictly examined conditions of culture growing the samples on the plates, and as a result, an apparatus for monitoring the luminescence of the organism samples according to the invention has been accomplished.

The apparatus for monitoring the luminescence of the organism samples according to the invention comprises a culture part including a plurality of plates for putting plural organism samples and capable of cultivating said plural organism samples, a monitoring part for monitoring the bioluminescences of said plural organism samples, a convey means for conveying said plural plates to said monitoring part, a control part for controlling a movement of said convey means and controlling a monitoring condition of the bioluminescence of said organism sample, and a computer for record and analysis, wherein said monitoring part, control part and computer are separated from each other.

In a preferable embodiment of the invention, the organism sample is an organism sample requiring a light for cultivation or an organism sample requiring no light for cultivation.

In another preferable embodiment of the invention, the plural plates circulate in said apparatus for monitoring the luminescence.

In the other preferable embodiment of the invention, the plural plates are set on the convey means.

In a further preferable embodiment of the invention, each of the plural plates comprises a well plate body having a plurality of well parts for putting the organism samples, and a sheet affixed onto an upper face of the well plate body for sealing the openings of the well parts.

In a still further preferable embodiment of the invention, said convey means is provided with a sensor detecting the plural plates.

In another preferable embodiment of the invention, said sensor is a light sensor.

In the other preferable embodiment of the invention, said sensor precisely determines a relative position between a photoelectron amplifier tube as a bioluminescence detector in the monitoring part and said plate.

In a further preferable embodiment of the invention, said convey means comprise a belt conveyor, a plate feeding machine, and a plate pushing machine.

In a still further preferable embodiment of the invention, said control part controls the monitoring of each organism sample at a constant time interval.

In another preferable embodiment of the invention, said monitoring condition is a condition selected from the group consisting of a waiting time for monitoring, a monitoring time, a standby time each cycle and the number of cycles.

In the other preferable embodiment of the invention, the organism sample is monitored within a temperature range of from 15° C. to 50° C.

In a further preferable embodiment of the invention, said apparatus further comprises a fan.

The apparatus for monitoring the luminescence of the organism sample according to the invention develops an advantageous effect that the organism samples can be monitored within a wide temperature range because the monitoring part is separated from a part being weak to heat.

Further, the apparatus for monitoring the luminescence of the organism sample according to the invention develops an advantageous effect that the bioluminescence of the plant can be monitored uniformly. That is, according to the invention, the reliable monitored result can be provided because the condition for culturing the organism sample on the plate can be set uniformly.

Also, the apparatus for monitoring the luminescence of the organism sample according to the invention develops an advantageous effect that the apparatus can be miniaturized as compared with the conventional apparatus.

BRIEF DESCRIPTION OF THE DRAWINGS

The invention will be described with reference to the accompanying drawings, wherein:

FIG. 7 is a detail view of a monitoring darkroom wherein FIG. 7A shows an embodiment of the structure of the positioning tray and FIG. 7B shows an embodiment of the structure of photoelectron amplifier tube and up-down mechanism and FIG. 7C shows an embodiment of positions of the photoelectron amplifier tubes and the movement of the positioning tray;

FIG. 11 shows a counting efficiency of the photoelectron amplifier tube wherein FIG. 11A plots counting values of eight photoelectron amplifier tubes when the bioluminescence is monitored using a luciferase reagent and FIG. 11B shows a counting value of back ground and a counting value of the photoelectron amplifier tube at each amount of luciferase;

FIG. 14 shows a uniformity every each well of the monitored result of the bioluminescence on the bioluminescence reporter strain CAB2::LUC of *Arabidopsis* wherein FIG. 14A shows a relative value of an amount of the bio-luminescence in each well and FIG. 14B shows a cycle of the bioluminescence rhythm;

FIG. 16 is a photograph showing an overview of an embodiment of the apparatus for monitoring the luminescence according to the invention.

DETAILED DESCRIPTION OF THE INVENTION

The apparatus for monitoring the luminescence of the organism samples according to the invention comprises a culture part including a plurality of plates for putting plural organism samples and capable of cultivating the plural organism samples, a monitoring part for monitoring the bioluminescences of the plural organism samples, a convey means for conveying the plural plates to the monitoring part, a control part for controlling the movement of the convey means and controlling a monitoring condition of the bioluminescence of the organism sample, and a computer for record and analysis, wherein the monitoring part, the control part and the computer are separated from each other, and enables the monitoring of the luminescence of the organism samples within a relatively wide temperature range. According to the conventional type monitoring apparatus, the monitoring is only carried out at a temperature of about 15-35° C. because the control part being weak to a high temperature and the computer for the record and analysis are arranged close to the so-called monitoring part. On the contrary, according to the invention, it is possible to conduct the monitoring even in a wide temperature range because the monitoring part, the control part and the like are separated from each other.

Figure 1:
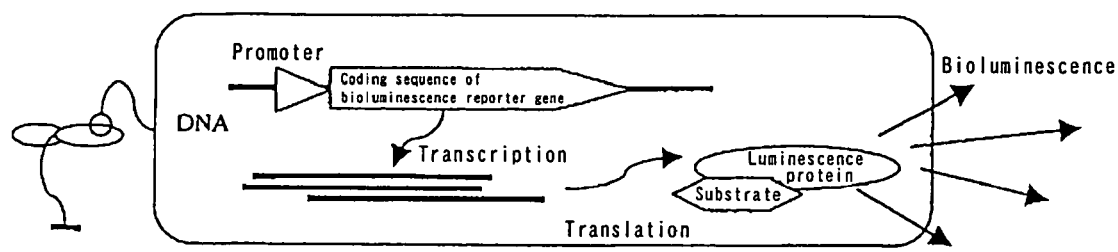
FIG. 1A is a schematic view of a bioluminescence reporter system.
FIG. 1B is a photograph of a bioluminescence reporter strain of *Arabidopsis* wherein the bioluminescence reporter strain CAB2::LUC of *Arabidopsis* grown on a solid medium is put into each well of a plate and sealed with a plate seal.
Figure 1:

The organism sample is not particularly limited, but may include an organism sample requiring a light for cultivation and an organism sample requesting no light for cultivation. Also, as the organism sample for monitoring the luminescence may be mentioned, for example, an organism sample incorporated with a gene having the bioluminescence property. The latter organism sample can be made by the gene manipulation. In a genome sequence of this recombined organism sample, a luminous gene such as luciferases from a firefly is incorporated into back of a promoter region for controlling the gene expression of the gene, so that a transcriptional activity of the promoter can be monitored as the bioluminescence in a living cell in real time (FIG. 1A).

Also, the plural plates are not particularly limited. For example, as the plate for storing the organism sample may be used the conventionally known 96-well plate and the like. In this case, an organism sample such as the above recombined organism or the like can be put into the 96-well plate and sealed with a transparent seal for using as a monitoring sample (FIG. 1B).

The culture part is set so as to cultivate the organism sample such as a plant or the like under uniform conditions, wherein the organism sample is stored in a well of each plate for storing the organism sample. For example, in the case that the light condition is made uniform, a light is uniformly irradiated from a light source (not shown) located above the culture part to cultivate the organism sample under constant culturing conditions.

In a preferable embodiment of the invention, the plural plates circulate in the apparatus for monitoring the bioluminescence. That is, when the plural plates circulate in the apparatus, particularly in a region of the apparatus setting suitable growth conditions such as irradiation from a light source and the like, it is possible to give substantially uniform growth conditions for cultivation to the organism sample placed in the apparatus. Such a circulation is preferable to be usually carried out along an inner periphery in the apparatus from a viewpoint of the provision of uniform growth conditions, but the approach for the circulation is not particularly limited. In brief, the approach is not particularly limited as long as the uniform growth conditions (for example, a light condition, a temperature condition, a humidity condition and the like) can be given to the organism sample.

In the invention, it is further preferable to set the plural plates on the convey means. In this case, an arm for conveying to the monitoring part is not required as long as the plate is set on the convey means. If the convey means is designed so as to circulate in the apparatus, there is a merit that the uniform growth conditions can be given to the organism samples. Also, the form or the like of the plural plates is not particularly limited, but the plate is preferable to be comprised of a well plate body having a plurality of wells for storing the organism sample and a sheet covering the upper surface of the well plate body for sealing the openings of the well parts from a viewpoint of the prevention of the dew formation in the well parts. Moreover, since the plates placed on the set part of the monitoring apparatus are immediately fed to the monitoring darkroom by the convey means, the plate prevented from the dew formation is subjected to the monitoring at a dew-free state.

Each of the plural plates for storing the organism samples comprises a well plate body having a plurality of wells for storing the organism samples and a sheet covering the upper surface of the well plate body for sealing the openings of the well parts, which is well-known as a 96-well plate or the like and is commercially available. If the culture part is constructed so that a bottom face temperature of the plate for storing the organism sample to be set on the culture part is made lower than a temperature of the sheet on the upper surface of the well plate body, the dew formation in the interior of the well covered with the sheet can be prevented more surely and hence reliable monitored results can be obtained.

Also, the culture part is provided with an air blowing fan for preventing the dew formation, whereby the bottom face temperature of the plate placed on the set portion of the culture part can be made lower than the temperature of the sheet on the upper surface of the plate to prevent the dew formation in the interior of the well part covered with the sheet. For example, the fan can be properly arranged in the inside of the apparatus comprising the culture part, the monitoring part, the convey part and the control part. The fan can be properly arranged in a space area around a power source, in the vicinity of a control substrate or the like.

Furthermore, the convey part may be provided with a sensor for detecting the plural plates. This sensor is to identify the position of the plate and can confirm the presence or absence of the plate at a particular position. The positioning of the plate can be precisely conducted by the sensor. Also, the sensor can adequately determine the relative position between the plate and the photoelectron amplifier tube as a luminescence detector in the monitoring part.

In the other preferable embodiment, the convey part is constituted with a belt conveyor, a machine for feeding the plate and a machine for pushing the plate. The details of them will be explained later. Furthermore, the operation of the control part for controlling the convey means will also be explained later.

Next, the control part will be explained. The control part mainly controls the conveying operation and the monitoring condition of the bioluminescence. That is, the control part is set so that the operation control of the convey part, command of monitoring start to the monitoring part and the like can be carried out by a control computer. The operation of the culture part and the convey part can be carried out, for example, by using a touch panel. The conveying operation allows the monitoring of each organism sample at a constant time interval. As the monitoring condition may be mentioned a condition selected from the group consisting of a waiting time for monitoring, a monitoring time, a standby time every cycle and the number of cycles.

A central part of the apparatus is a monitoring darkroom in which shutters 1 and 2 are attached to both an enter port and discharge port for the plate. By arranging a positioning tray and a light sensor in the darkroom can be strictly controlled a relative position between a photoelectron amplifier tube and a sample plate.

The following examples are given in illustration of the invention and are not intended as limitations thereof.

Figure 2:
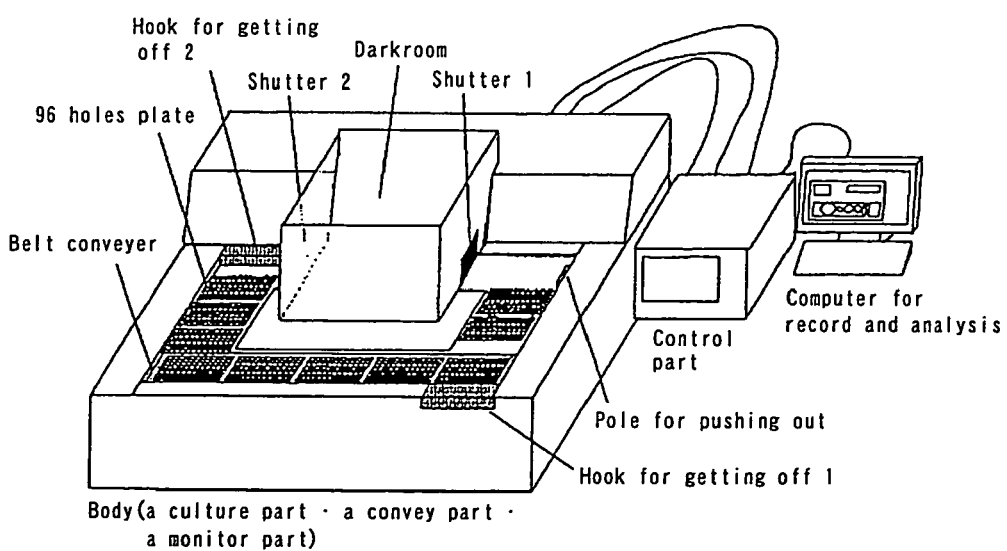
FIG. 2 is a diagrammatic view of an apparatus for monitoring a bioluminescence with a circulation-type exchanger of organism samples.

The monitoring apparatus according to the invention has the following characteristics; that is, (1) the positions of the samples to be monitored can be sequentially changed by adopting a circulation system as a conveying system during the operation of the apparatus to uniformize cultivating and monitoring conditions, (2) the miniaturization can be attained by rendering the conveying mechanism of the plant sample into a circulation system so as to keep with the culture part, and (3) the operation can be conducted under a wide temperature environment (at least 15-50° C.) by separating the control part and the computer for record/analysis from the main body of the apparatus (constituted with the culture part, the convey part of the sample and the monitoring part). The outline of the monitoring apparatus according to an embodiment of the invention is shown in FIG. 2. Furthermore, a photograph of the external appearance of the apparatus is shown in FIG. 16.

Figure 5:
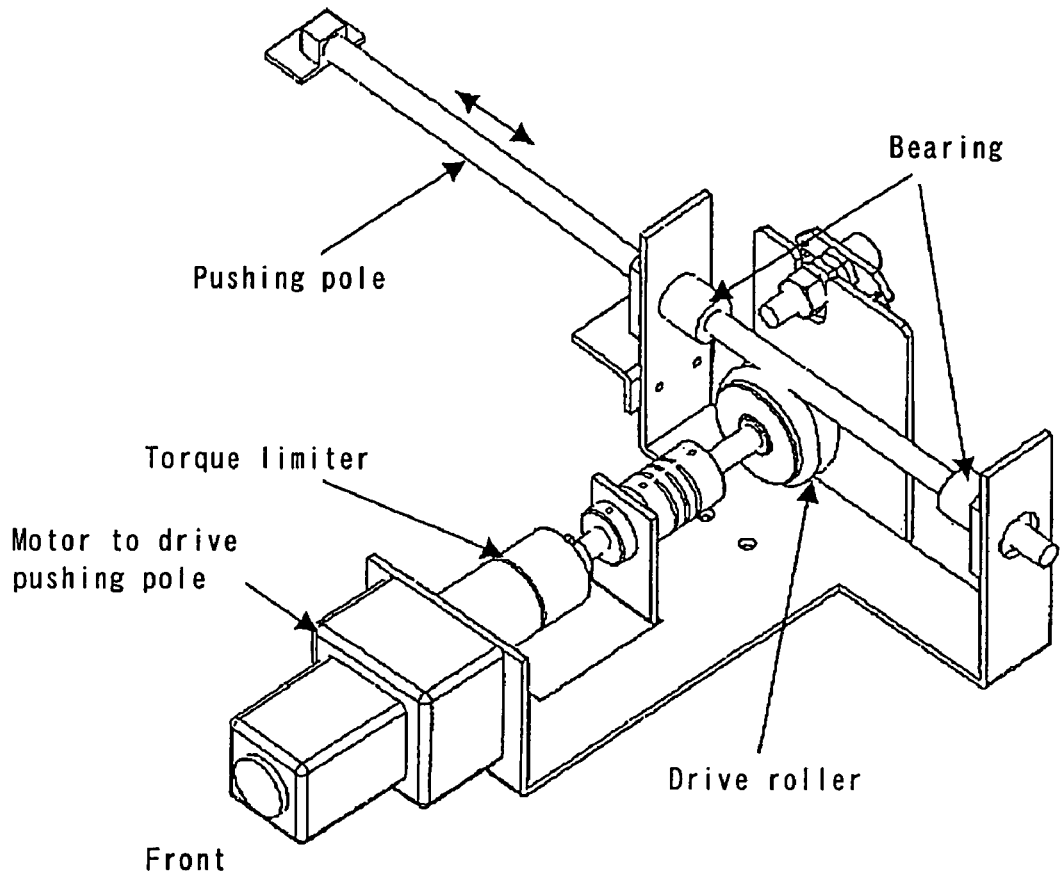
FIG. 5 is a detail view of a plate pushing bar.
Figure 6:
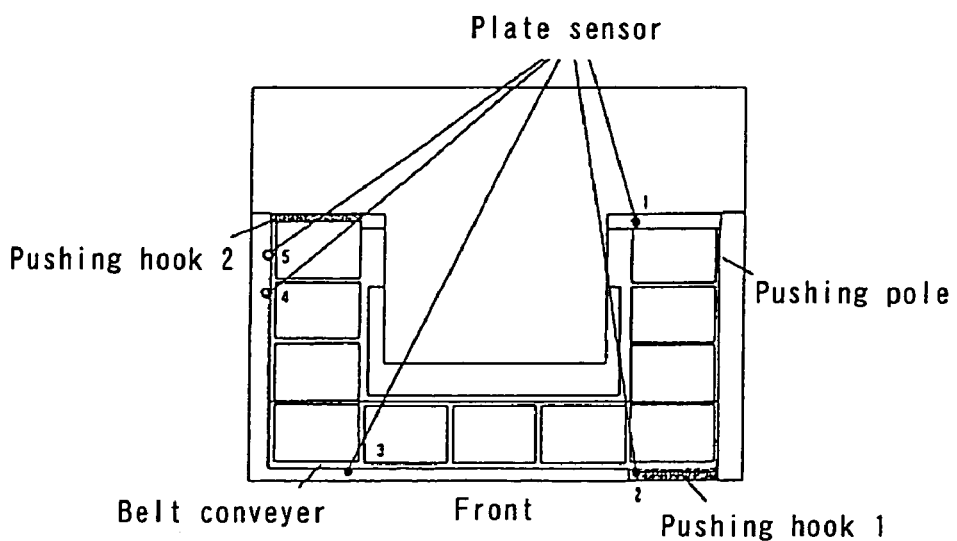
FIG. 6 is a view illustrating an embodiment of a position of a positioning sensor in a convey means in which positions of light sensors for confirming positions of plates in the conveying are shown by black circles 1-4 and a part related to the movement of the plate is shown and a blue color shows a belt conveyor.

The convey part is constituted with a belt conveyor (FIG. 3), a plate feeding bar (FIG. 4), a plate pushing bar (FIG. 5) and a position sensor (FIG. 6).

Figure 7:
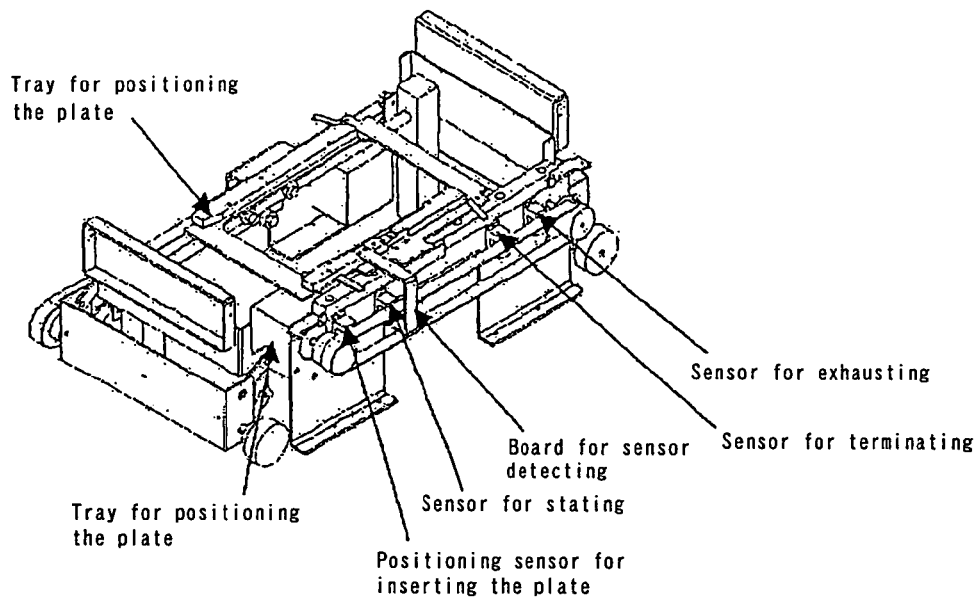
Figure 7:
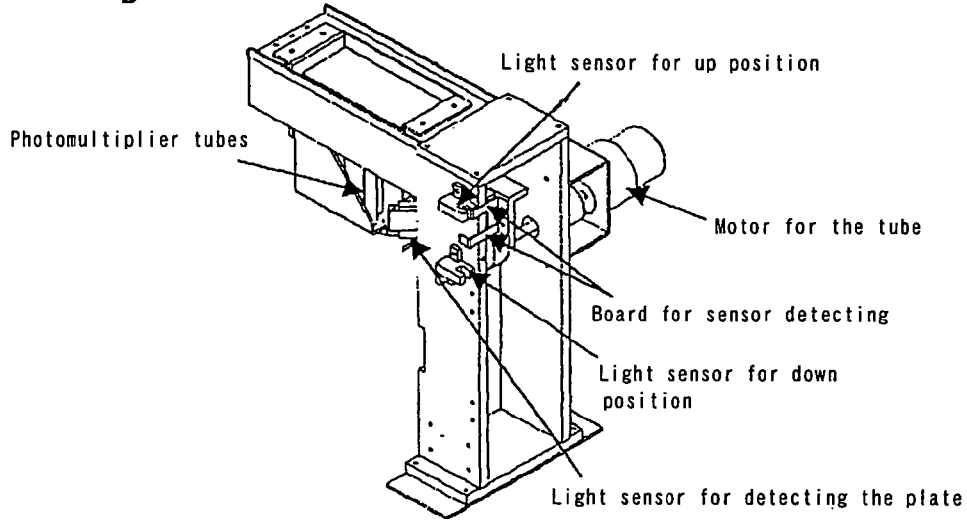
Figure 7:
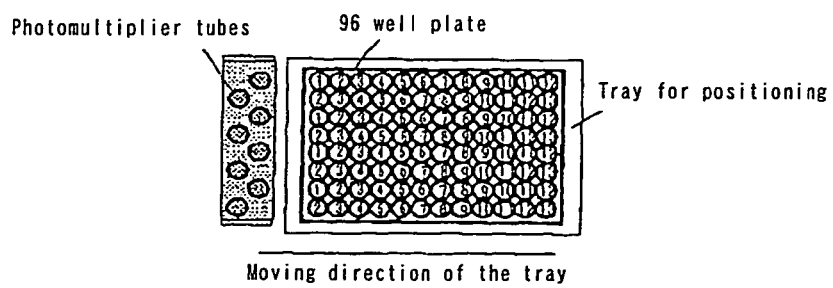

By arranging a positioning tray and a light sensor in the monitoring part can be strictly controlled a relative position between a photoelectron amplifier tube and a sample plate (FIG. 7).

A miniaturization and a weigh reduction of the apparatus are achieved by combining the culture part of the sample-to be monitored with the convey part and integrally uniting the monitoring part with the culture-convey part.

By separating the control part being weak to a high temperature and the computer for record and analysis from the main body of the apparatus (comprising the culture part, the convey part and the monitoring part) (FIG. 2) can be conducted the monitoring of at least 15-50° C. Moreover, the main body (culture part, convey part and monitoring part) of the apparatus prototyped in the invention has a size of 68 cm in length, 93 cm in width and 36 cm in height and a weight of 50 kg, which is a considerably small and light weigh apparatus as compared with this type of the conventional apparatus.

Use Method and Operation of the Apparatus

Figure 3:
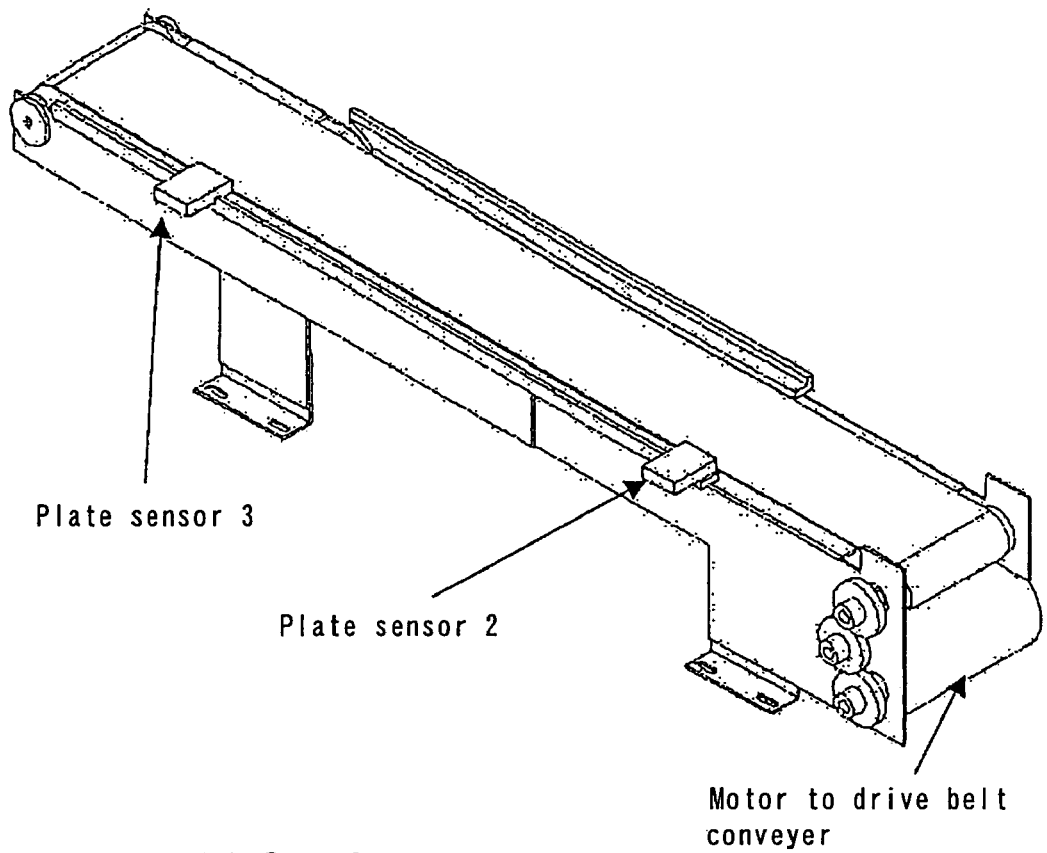
FIG. 3 is a detail view of a belt conveyor.
Figure 4:
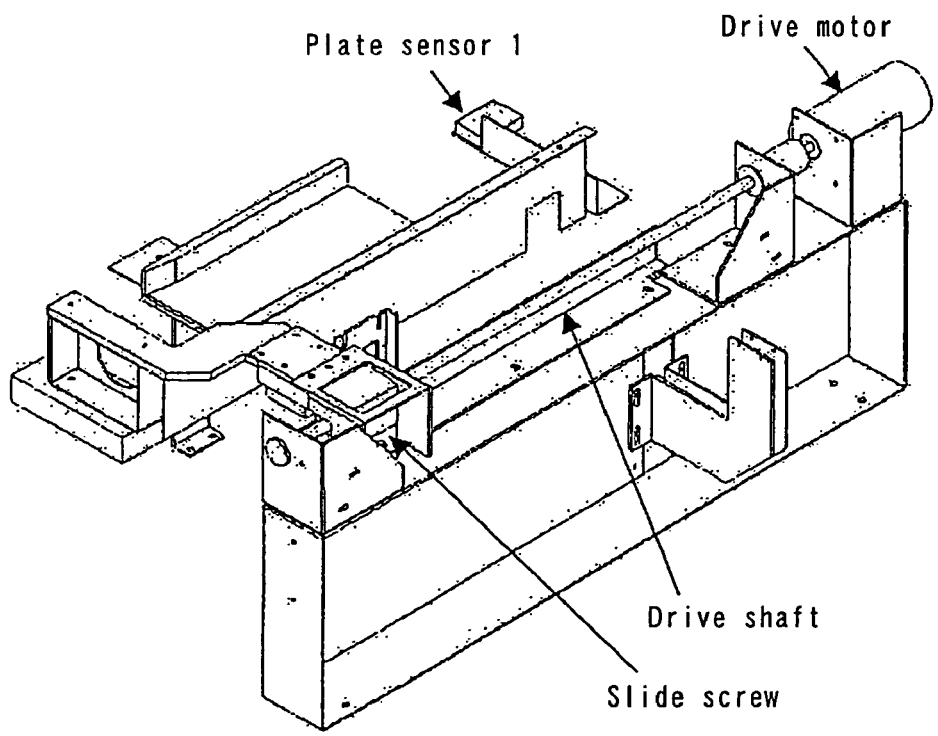
FIG. 4 is a detail view of a plate feeding bar.
Figure 8:
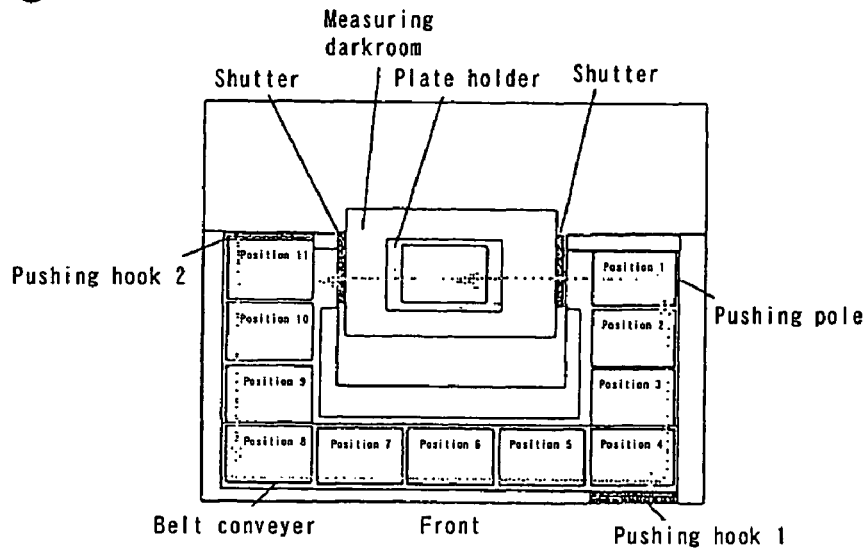
FIG. 8 is a schematic view illustrating a monitoring operation of the apparatus in which parts related to the movement of the plate during monitor and the position of the plate are shown and an arrow of orange color shows the movement of the plate during the monitoring and a blue color shows a belt conveyor.
Figure 9:
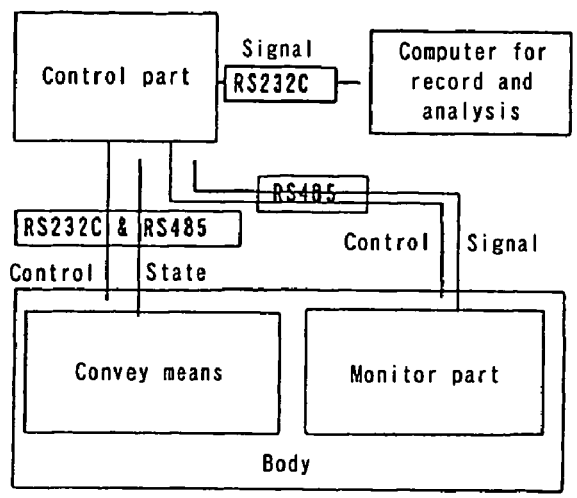
FIG. 9 is a schematic view of an embodiment illustrating a connection between parts in the apparatus and a signal transfer pathway.

Ten 96-well plates including samples to be monitored (Culture plate-96; Perkin Elmer Life Sciences Japan, Tokyo or analogous thereof, hereinafter referred to as plate) are set at plate positions 2-11 of FIG. 8. The monitoring is started by inputting the monitoring conditions (a waiting time for monitoring, a monitoring time, a standby time every cycle, the number of cycles) to the control part (FIG. 8). A drive motor for the plate feeding bar (machine) moves a plate feeding bar 1 through a drive shaft and a slide screw to feed the plates of positions 2-4 to positions (positions 1-3) of the back of the culture part (FIG. 4). A drive motor for plate positioning tray set in the monitoring darkroom moves a plate positioning tray to a plate inserting position after the plate positioning tray is positioned by a sensor for plate inserting position and a sensor detecting board (FIG. 7A). As the drive motor for the plate positioning tray is used a stepping motor. As the existence of the plate at position 1 is confirmed by a light sensor 1 for detecting the plate position (FIG. 6), both shutters 1 and 2 of the monitoring darkroom are opened. A drive motor for plate pushing bar (machine) moves a plate pushing bar through a drive roller feed the plate of position 1 to the plate positioning tray (FIG. 5). The plate pushing bar is returned to a standby position, and the shutters 1 and 2 of the darkroom for monitoring are closed. As the absence of the plate at position 4 is confirmed by a light sensor 2 for detecting the plate position, a drive motor for a belt moves a belt conveyor to transfers the plates of positions 5-8 to a right side (positions 4-7) of the apparatus (FIG. 3). As the absence of the plate at position 8 is confirmed by a light sensor 3 for detecting the plate position, a plate feeding bar 2 send the plates of positions 9-11 to a front side of the culture part (positions 8-10). Plate position sensors 4 and 5 confirm that the plate of position 11 moves to position 10. The plates in the monitoring darkroom are left to stand at rest under blackness for an arbitrary time (0-999.9 minutes) and thereafter a luminescence of each well in the plates is monitored by a photoelectron amplifier tube. The luminescence monitoring of each well in the plates is carried out by 8 photoelectron amplifier tubes alternately assigned each other (FIGS. 7B, 7C). The drive motor for the plate positioning moves the plate positioning tray to a monitoring start position after the position of the plate positioning tray is determined by a sensor for a monitoring start position. At the monitoring start position, the plate becomes under the photoelectron amplifier tube. A lifting motor for the photoelectron amplifier tube is driven to descent the photoelectron amplifier tube. When a light sensor for detecting a down-position of a detector detects a sensor detecting board, the lifting motor for the photoelectron amplifier tube is stopped to contact the photoelectron amplifier tube with the plate. A plate position detecting sensor (FIG. 7B) confirms the existence of the plate at the monitoring position. The photoelectron amplifier tube monitors the luminescence. The monitored value is sent from the monitoring part to the control part through RS485 every the monitoring of each well. After the monitoring, the lifting motor for the photoelectron amplifier tube is driven to raise the photoelectron amplifier tube. As a light sensor for detecting an up-position of the detector detects the sensor detecting board, the lifting motor for the photoelectron amplifier tube is stopped. The drive motor for the plate positioning tray moves the tray by driving only a step number required for transferring the plate to a monitoring position of a next line. By repeating such an operation are monitored all wells of 12 lines. At a time of completing all wells of the plate, the existence of the plate at a monitor terminating position is confirmed by a sensor for the monitor terminating position, and thereafter the monitored values are sent from the control part to the computer for record and analysis through RS232 together with the transmitted date and hour (FIG. 9). The monitored values are recorded in the computer for record and analysis as a CVS file every the plate together with the transmitted date and hour of monitoring data. The drive motor for the plate positioning tray moves the plate positioning plate to a plate discharge position after the position of the tray is determined by a sensor for the plate discharge position. After the completion of the monitoring on one plate, the absence of such a plate at position 11 (FIG. 8) is confirmed by the light sensors 4 and 5 for detecting the plate position (FIG. 6). Both the shutter 1 and 2 of the monitoring darkroom are opened to discharge the plate in the darkroom to the position 11 of the culture part through the pushing bar. Then, the shutter 1 and 2 are closed.

A series of these operations are automatically repeated at a time interval set by the experimenter. The visualization and analysis of the monitored data are automatically carried out by an analyzing program installed in the computer for record and analysis (Japanese Patent Application No. 2003-061203 filed by Okamoto et al.).

At first, a luminescence detecting sensitivity and a linearity of the apparatus are examined. As a luminous sample are used luciferase (QuantiL um Recombinant Luciferase, Promega Corp.) and a solution of a luminous substrate (Steady-Glo Luciferase Assay System, Promega Corp.). A solution of $1.33 \times 10^{-16}$–$1.33 \times 10^{-9}$ M luciferase and the solution of luminous substrate are mixed at an equal volume while cooling on ice, and the resulting reaction solution is poured into each well of the plate set on ice at an amount of 150 µl, and these wells are sealed with a transparent plate seal (Top Seal-A, Perkin Elmer Life Science). After 20 minutes of the mixing, the plate is rendered into 22° C. After the temperature of 22° C. is kept for 30 minutes, the plate is transferred to the darkroom and left to stand at rest for 5 minutes, and then the monitoring is started. The monitoring is carried out for 5 seconds on each well.

The results are shown below. The evaluation of the apparatus is carried out by examining a counting efficiency of 8 photoelectron amplifier tubes incorporated in the monitoring apparatus, a range of measurable bioluminescence amount, and a linearity of the monitored value for the bioluminescence amount with in-vitro luminescence system using a luciferase protein.

Figure 11:
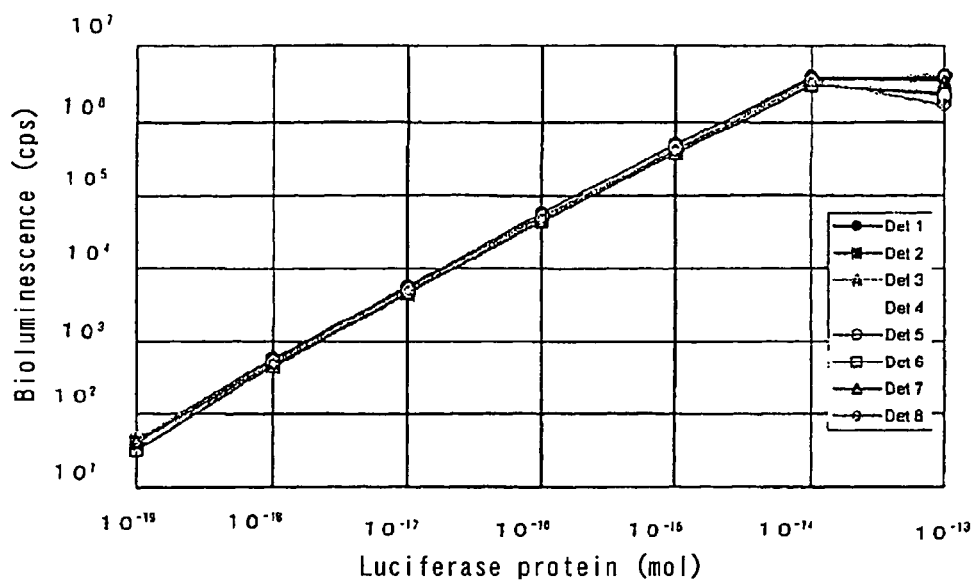

The counting value of back ground having no luciferase protein is 66±12 cps. When the amount of luciferase protein is $1.0 \times 10^{-19}$–$1.0 \times 10^{-14}$ mol, the counting value linearly increases in proportion to the amount of luciferase protein, and $4.3 \times 10$–$3.4 \times 10^6$ cps is counted (FIG. 1A). When the amount of luciferase protein is $1.3 \times 10^{-13}$ mol, a counting loss of a light quantum is caused and hence the counting no longer lineally increases. As seen from the above, a detecting sensitivity of the luminescence monitoring in the apparatus is $2.0 \times 10^{-19}$ mol of luciferase protein, and a dynamic range thereof is $4.3 \times 10$–$3.4 \times 10^6$ cps. A standard deviation of the counting efficiency of 8 photoelectron amplifier tubes is not more than 11% within the measurable range. A standard deviation of the monitored result of each photoelectron amplifier tube every luciferase concentration is 2% on average (FIG. 11B).

EXAMPLE 2

Next, there is examined an influence of a temperature on the monitoring sensitivity. As a standard light source is used CXS-2011 made by Aloka Co., Ltd. After the standard light source is placed in the well of the plate, a counting value of the well is monitored under temperature environments of 15, 20, 25, 30, 35, 40, 45 and 50° C.

Figure 12:
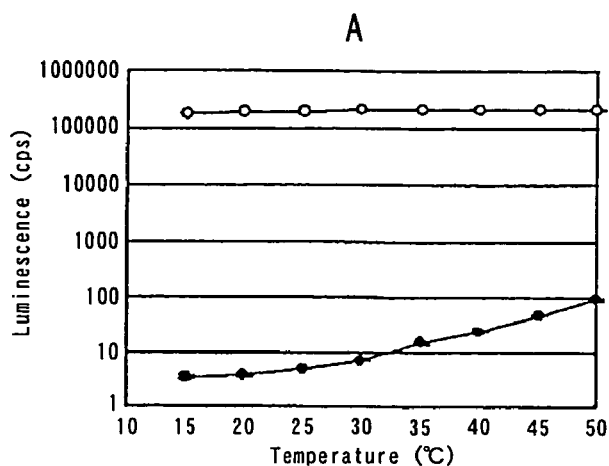
FIG. 12 shows an influence of a temperature on the monitoring sensitivity.

The results are as follows. In order to clarify what temperature range can be used in the apparatus for monitoring the luminescence according to the invention, the luminescence is monitored under various temperature conditions about the main body of the apparatus (the culture part, the convey part and the monitoring part) (FIG. 12). When the monitoring temperature is raised from 15° C. to 50° C. every 5° C., the counting value of the background increases from 3 cps to 90 cps. On the other hand, the counting value of the standard light source is constant at $2.0 \times 10^5$ cps. As seen from this result, the monitoring of the luminescence in the apparatus can be carried out within a temperature range of 15-50° C.

EXAMPLE 3

The monitoring of a bioluminescence reporter strain of *Arabidopsis* is carried out below. As a sample for monitoring the bioluminescence is used a bioluminescence reporter strain CAB2::LUC of *Arabidopsis*. (Millar et al., 1992, Plant Cell Vol. 4, p 1075-1087). This stain is a stain wherein a luminescence reporter gene connected a region for encoding luciferase gene LUC of a firefly down the stream of the promoter region of CAB2 gene of *Arabidopsis* encoring a chlorophyll a/b binding protein is transfused to a genome of a wild type strain C24, and shows a bioluminescence rhythms with period lengths of about 24 hours under constant light condition by being controlled with a circadian clock. Also, the strain shows a decrease of an amount of the bioluminescence and an elongation of the period of the rhythms of the bioluminescence when a light intensity irradiated during culture is decreased. (Millar et al., 1992, Plant Cell Vol. 4, p 1075-1087; Somers et al., 1998, Development Vol. 125, p 485-494).

Figure 10:
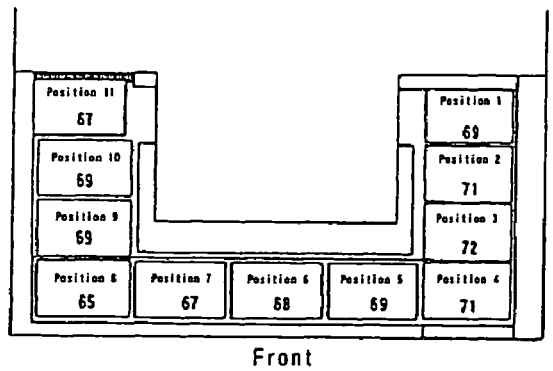
FIG. 10 is a view showing an amount of a light irradiated to the luminescence reporter strain CAB2::LUC of *Arabidopsis* at each position (positions 1-11) (numerical value beneath position number, unit: μmol m$^{-2}$s$^{-1}$)

The rhythms of the bioluminescence about CAB2::LUC strain is monitored as follow. After seeds derived from a surface-sterilized CAB2::LUC strain are left at 4° C. under blackness for 2 days to conduct a treatment of tuning the gammadion, they are seeded in a solid culture (MS culture) of Murashige and Skoog containing 1.5% of sucrose and 0.3% of germain gam and germinated by cultivating at 22.0±0.5° C. under the white light of 50 µmol m$^{-2}$ s$^{-1}$ in constant light for 4 days. In each well of ten plates is poured 20 µl of the MS liquid culture containing 1.5% of sucrose, and a germ of the plant cutout together with the solid culture is transferred to the well. Furthermore, 20 µl of an aqueous solution of 500 µM D-luciferin (BIOSYNTH AG, Staad, Switzerland) is added to each of the wells, and the plate is sealed with a plate seal, and then a circadian clock is tuned by subjecting to a light-dark cycle comprising a light period for 12 hours and a dark period for 12 hours (irradiation of 70 µmol m$^{-2}$ s$^{-1}$ of a white light in the light period) at 23.0±0.5° C. 3 cycles. Just after the completion of the third dark period, the plate is set to the monitoring apparatus, and a white light is continuously irradiated thereto at 23.0±0.5° C. An amount of the white light irradiated to each position of the plate is shown in FIG. 10. An average amount of the white light at all positions of the plate is 68.8±2.0 µmol m$^{-2}$s$^{-1}$ and is uniform.

After the plate is left to stand in the monitoring darkroom at rest for 4 miniatures under the darkness to attenuate a delayed fluorescence of chlorophyll of the plant, the monitoring of the bioluminescence every well is carried out under the darkness for 3 seconds to record the result as a value of the bioluminescence per second, This monitoring is repeated every 90 minutes. The data of the bioluminescence value are analyzed by using a data-analyzing software RAP to conduct the evaluation on the luminescence intensity and the variation of luminescence amount (rhythm of the luminescence).

Figure 13:
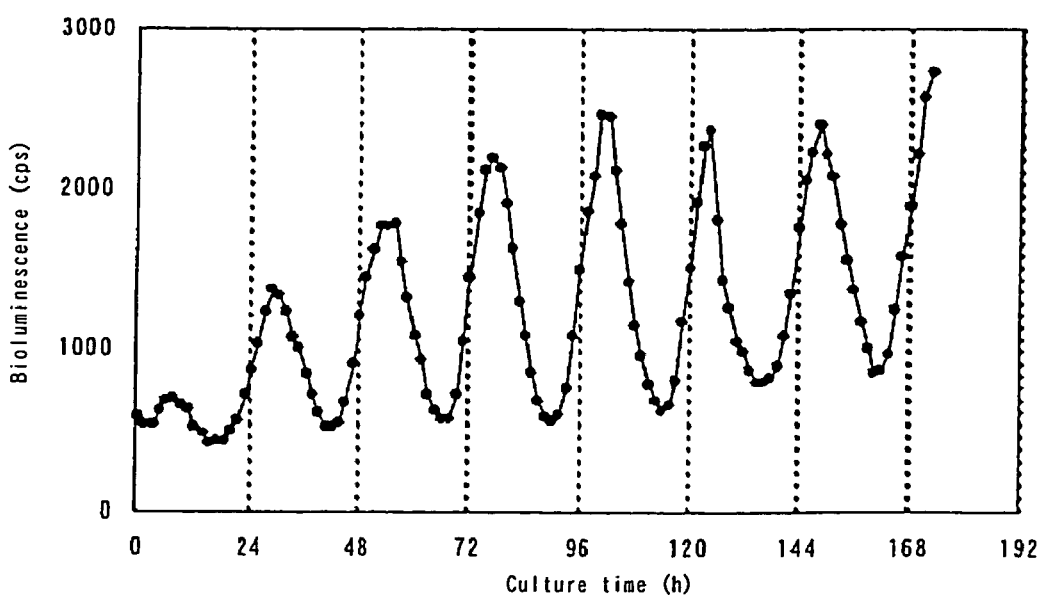
FIG. 13 shows a bioluminescence rhythm of bioluminescence reporter strain CAB2::LUC of *Arabidopsis*.
Figure 14:
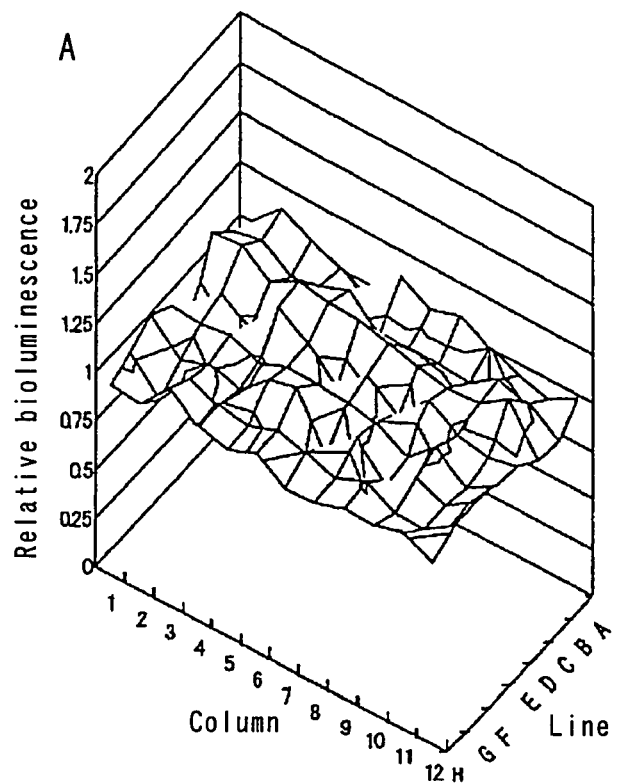
Figure 14:
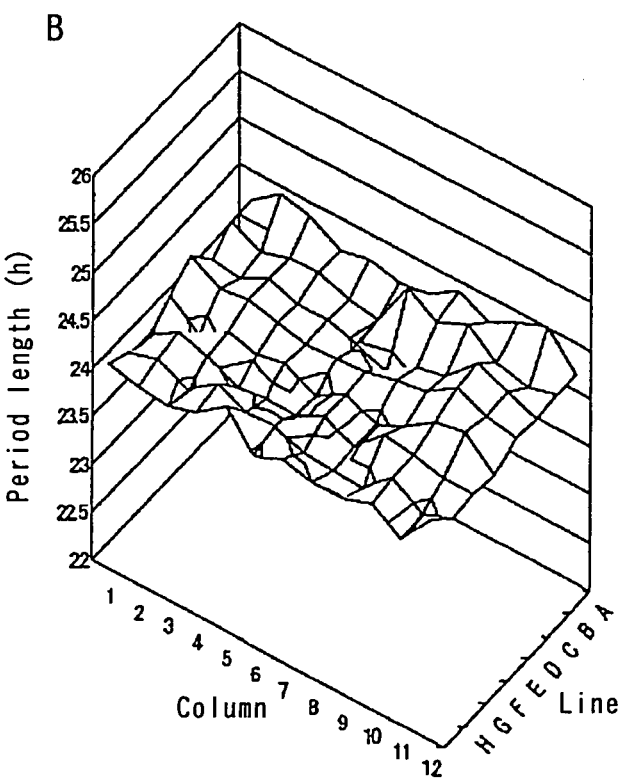

The monitored result on the luminescence reporter strain of *Arabidopsis* is as follows. The bioluminescence amount and the uniformity of the period of the rhythm are examined by monitoring the rhythm of the bioluminescence about the luminescence reporter strain CAB2:LUC of *Arabidopsis* through the apparatus for monitoring reporter luminescence according to the invention (FIG. 13). The bio-luminescence amount is 1,532±112 cps every well (FIG. 14A) and 1,532±297 cps every plate (Table 1) and the value is even. Table 1 shows the uniformity of the monitored result of the luminescence reporter strain CAB2:LUC of *Arabidopsis* every plate.

TABLE 1

| | Bioluminescence * | | Period length * | |
|---|---|---|---|---|
| Plate number | Photon count (cps) | Relative value | (h) | n |
| 1 | 1.505 ± 274 | 0.98 ± 0.18 | 24.03 ± 0.28 | 90 |
| 2 | 1.557 ± 237 | 1.02 ± 0.15 | 24.08 ± 0.26 | 85 |
| 3 | 1.456 ± 287 | 0.95 ± 0.19 | 24.19 ± 0.44 | 76 |
| 4 | 1.577 ± 300 | 1.03 ± 0.20 | 24.10 ± 0.40 | 83 |
| 5 | 1.627 ± 333 | 1.06 ± 0.22 | 24.00 ± 0.36 | 84 |
| 6 | 1.558 ± 278 | 1.02 ± 0.18 | 24.09 ± 0.34 | 77 |
| 7 | 1.476 ± 282 | 0.96 ± 0.18 | 24.23 ± 0.38 | 80 |

TABLE 1-continued

| Plate number | Bioluminescence * | | Period length * (h) | n |
|---|---|---|---|---|
| | Photon count (cps) | Relative value | | |
| 8 | 1.500 ± 262 | 0.98 ± 0.17 | 24.16 ± 0.35 | 68 |
| 9 | 1.649 ± 273 | 1.08 ± 0.18 | 24.08 ± 0.27 | 83 |
| 10 | 1.358 ± 354 | 0.89 ± 0.23 | 24.40 ± 0.41 | 63 |
| Mean | 1.532 ± 297 | 1.00 ± 0.19 | 24.14 ± 0.36 | 789 |

* Values are mean ± SD

The period of the rhythm of the bioluminescence is 23.2±0.4 h every well (FIG. 14B) and 23.2±0.4 h every plate (Table 1) and the value is even.

EXAMPLE 4

The monitoring of the luminescence is carried out by using a luminescence reporter strain of thermophilic blue-green bacterium.

A psbA1 luminescence reporter strain of *thermosynechococcus elongates* is used. This strain is a strain wherein a luminescence reporter gene connected to the luciferase gene operon (X1 luxAB) from *Xenorhabdus* luminescence belonging to thermoduric bacteria at the downstream of the promoter sequence of psbA1 gene of *T. elongates* is gene-transfused to the genome of the wild type. The rhythm of the bioluminescence can be observed by adding a luminous substrate to psbA1 luminescence reporter strain because the transcription activity of psbA1 gene varies in a daily periodicity and shows a circadian rhythm. A colony is formed by cultivating a cell of psbA1 luminescence reporter strain on BG-11 solid medium at 52° C. under a continuous irradiation of a white light of 50 µmol m$^{-2}$ s$^{-1}$. In each well of the plate is poured 20 µl of BG-11 liquid medium, and the colony (1 or more) cutout together with the BG-11 solid medium is fed in the well. Further, 20 µl of n-decanal dissolved in a salad oil at a concentration of 0.1% is fed in a well close to the well including the colony, and then the plate is sealed with a plate seal. N-decanal as a luminous substrate for a bacteria luciferase is volatile and is vaporized in the plate to permeate from a gas phase into the cell. In order to tune a biological clock, the plate is left to stand at 41° C. under the dark condition for 12 hours. Thereafter, the plate is set to the apparatus of monitoring the luminescence according to the invention to monitor the luminescence while cultivating the cell at 41° C. under a continuous irradiation of a white light of 50 µmol m$^{-2}$ s$^{-1}$. After the plate is left to stand in the monitoring darkroom under the darkness for 3 minutes to attenuate a delayed fluorescence of chlorophyll, the monitoring of the bioluminescence is carried out under blackness for 3 seconds to record the result as a value of the bioluminescence per second. An analysis of the monitored data is carried out by using a data analyzing software RAP.

The monitored result of psbA1 luminescence reporter of the thermophilic blue-green bacterium, *T. elongatus* is shown below.

Figure 15:
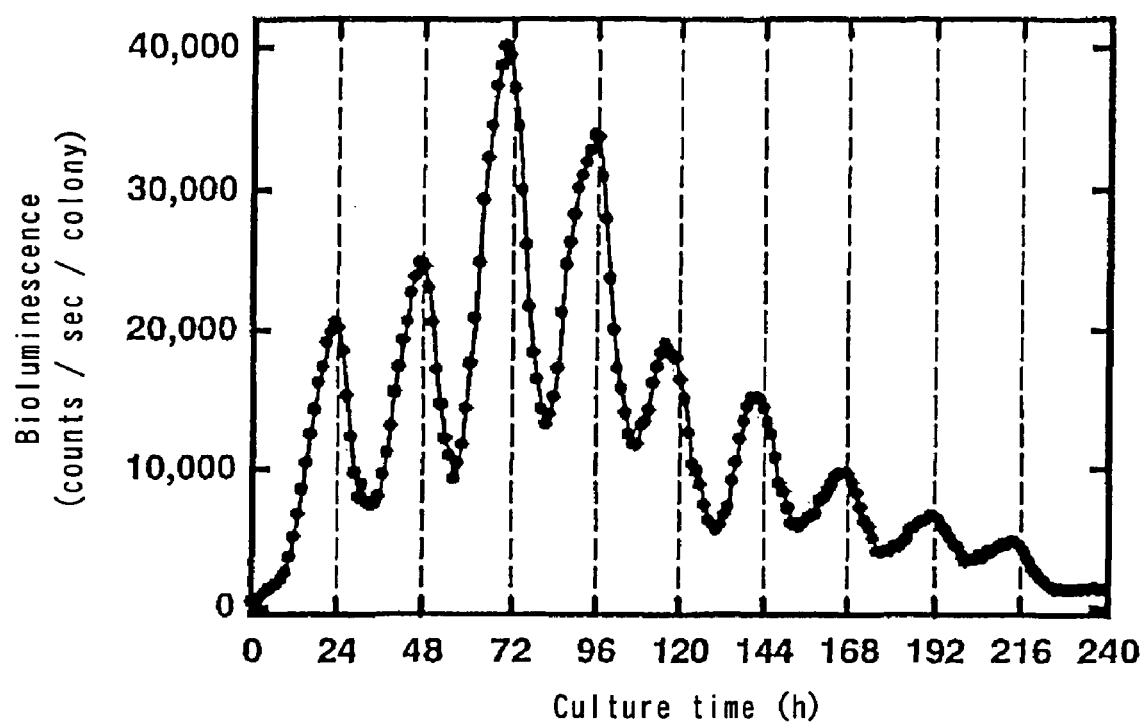
FIG. 15 shows a bioluminescence rhythm of psbA1 luminescence reporter strain of thermophilic blue-green bacterium *T. elongates*.

While psbA1 luminescence reporter strain of *T. elongatus* is cultivated at a high temperature of 41° C., the monitoring is carried out by the apparatus for monitoring the luminescence according to the invention to successfully monitor the rhythm of the bioluminescence of this strain (FIG. 15). The continuous measurement of the rhythm for at least 10 days can be achieved. As seen from this result, the continuous measurement over a long time even at the high temperature of 41° C. can be achieved by using the apparatus of the invention.

In the invention, since the monitoring part is separated from the control part, the monitoring of the bioluminescence of the plant in large-scale and the monitoring of the bioluminescence within a wide temperature range of at least 15-50° C. can be attained. Also, it is clarified that the invention has the following three features.

By rendering the conveying system of the sample into a circulation system can be attained the cultivation and the monitoring under uniform light conditions. That is, by adopting the circulation system as the conveying system can be uniformized the shifting of the position on the sample during the monitoring and the cultivating and monitoring conditions.

It has been found that the apparatus for monitoring the rhythm of the luminescence developed by the inventors can set ten 96-well micro-plates at maximum and monitor continuously and automatically the bioluminescence while cultivating 960 individual plants in one assay. Also, since a space required for arranging the apparatus of the invention is small as compared with the use of the usual scintillation counter, the apparatus of the invention can monitor the bioluminescence on a greater number of plants to be tested in the same experimental space. The uniformity on the luminescence intensity and the period of the rhythm obtained by the apparatus of the invention is much higher than the result obtained by an apparatus including a scintillation counter and a tabular culture-convey means, which has been previously developed by the inventors (Japanese Patent Application No. 2003-060069). This can be guessed due to the fact that the culture conditions on all plates are made uniform by circulating the plates.

Furthermore, it has also been found that the monitoring apparatus can conduct the monitoring under a condition of a temperature higher than that of the conventional monitoring apparatus because the control part being low in the heat resistance is separated from the cultivating and monitoring parts. By using the apparatus for monitoring the rhythm of the luminescence capable of operating under a high temperature condition up to at least 50° C. can be carried out the monitoring of the bioluminescence of thermophilic organisms under a temperature condition suitable for their growth. The inventors success the monitoring of the rhythm of the bioluminescence by incorporating a gene encoding a thermostable emission protein to a thermophilic blue-green bacterium, *Thermosynechococcus elongatus* BP-1.

Although all genome sequences are already determined in *Arabidopsis* or *elongatus* (The *Arabidopsis* Genome Initiative, 2000, Nature Vol. 408, p 796-815; Nakamura et al., 2000, DNA Res. Vol. 9, p 123-130), functions of greater part of genes are not yet settled. A large scale real-time analysis of the gene expression using the bioluminescence is considerably effective as a method of analyzing the function of the genome in post-genome age. The inventors believe that the developed apparatus for automatically monitoring the bioluminescence is very powerful tool in the large-scale analysis of the gene expression.

The method for real-time monitoring the bioluminescence, in which the variation of the gene expression is continuously monitored in a living cell of the organism incorporated with a luminous gene (FIG. 1A), is a very effective test method for the encompassing separation of the mutant related to the control of the expression of a random key gene, and is a master card for the encompassing analysis of the function of the genome in post-genome age. The invention is applicable in this type of analysis.

What is claimed is:

1. An apparatus for monitoring a luminescence of an organism sample comprising a culture part including a plurality of plates for putting plural organism samples and capable of cultivating said plural organism samples, a monitoring part for monitoring bioluminescences of said plural organism samples, a convey means for conveying said plural plates to said monitoring part, a control part for controlling a movement of said convey means and controlling a monitoring condition of the bioluminescence of said organism sample, and a computer for record and analysis, wherein said monitoring part, control part and computer are separated from each other, and said convey means comprises a belt conveyor, a plate feeding machine, and a plate pushing machine.

2. An apparatus according to claim 1, wherein the organism sample is an organism sample requiring a light for cultivation or an organism sample requiring no light for cultivation.

3. An apparatus according to claim 1, wherein the plural plates circulate in said apparatus for monitoring the luminescence.

4. An apparatus according to claim 1, wherein the plural plates are set on the convey means.

5. An apparatus according to claim 1, wherein each of the plural plates comprises a well plate body having a plurality of well parts for putting the organism samples, and a sheet affixed onto an upper face of the well plate body for sealing the openings of the well parts.

6. An apparatus according to claim 1, wherein said culture part constructed so that a bottom face temperature of the plate for storing the organism sample to be set on the culture part is made lower than a temperature of the sheet on the upper surface of the well plate body.

7. An apparatus according to claim 1, wherein said convey means is provided with a sensor detecting the plural plates.

8. An apparatus according to claim 7, wherein said sensor is a light sensor.

9. An apparatus according to claim 8, wherein said sensor precisely determines a relative position between a photoelectron amplifier tube as a bioluminescence detector in the monitoring part and said plate.

10. An apparatus according to claim 1, wherein said control part controls the monitoring of each organism sample at a constant time interval.

11. An apparatus according to claim 1, wherein said monitoring condition is a condition selected from the group consisting of a waiting time for monitoring, a monitoring time, a standby time each cycle and the number of cycles.

12. An apparatus according to claim 1, wherein the organism sample is monitored within a temperature range of from 15° C. to 50° C.

13. An apparatus according to claim 1, wherein said apparatus further comprises a fan.

* * * * *